(12) United States Patent
Gillard et al.

(10) Patent No.: US 10,213,315 B2
(45) Date of Patent: Feb. 26, 2019

(54) ATTACHMENTS FOR ORTHOPEDIC IMPLANTS

(71) Applicant: Zimmer, Inc., Warsaw, IN (US)

(72) Inventors: Duane Gillard, Pierceton, IN (US); James Richard Miller, Jr., Warsaw, IN (US); Stephen H. Hoag, Warsaw, IN (US); Justin S Hertzler, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 563 days.

(21) Appl. No.: 15/041,706

(22) Filed: Feb. 11, 2016

(65) Prior Publication Data

US 2016/0158022 A1 Jun. 9, 2016

Related U.S. Application Data

(63) Continuation of application No. 13/774,629, filed on Feb. 22, 2013, now Pat. No. 9,295,554, which is a (Continued)

(51) Int. Cl.
*A61F 2/42* (2006.01)
*A61F 2/30* (2006.01)
*A61F 2/46* (2006.01)

(52) U.S. Cl.
CPC ........ *A61F 2/4202* (2013.01); *A61F 2/30771* (2013.01); *A61F 2002/3092* (2013.01); (Continued)

(58) Field of Classification Search
None
See application file for complete search history.

(56) References Cited

U.S. PATENT DOCUMENTS 5,282,861 A 2/1994 Kaplan
6,361,731 B1 3/2002 Smith et al.
(Continued)

FOREIGN PATENT DOCUMENTS

WO WO-9515732 A1 6/1995

OTHER PUBLICATIONS

"U.S. Appl. No. 13/545,119, Restriction Requirement dated Dec. 31, 2014", 6 pgs.
(Continued)

*Primary Examiner* — Sameh Boles
(74) *Attorney, Agent, or Firm* — Schwegman Lundberg & Woessner, P.A.

(57) ABSTRACT

Apparatuses, kits, and methods for cementing an orthopedic implant to a bone, post attachment, are disclosed in some aspects of the present disclosure. A kit can include a prosthetic component and a cement applicator. The prosthetic component can include an attachment profile that corresponds to a mating profile formed on or in a bone. The cement applicator can be configured to apply a bone cement between the bone and the prosthetic component following alignment between the prosthetic component and the bone or another prosthetic component. The kit can also include a bone cement. A method can include positioning the prosthetic component adjacent to the bone, aligning the prosthetic component relative to the bone or another prosthetic component, and applying a bone cement between the bone and the aligned prosthetic component.

10 Claims, 7 Drawing Sheets

Related U.S. Application Data continuation-in-part of application No. 13/545,119, filed on Jul. 10, 2012.

(52) U.S. Cl.
CPC .......... A61F 2002/3093 (2013.01); A61F 2002/30599 (2013.01); A61F 2002/30622 (2013.01); A61F 2002/30736 (2013.01); A61F 2002/30883 (2013.01); A61F 2002/4205 (2013.01); A61F 2002/4207 (2013.01); A61F 2002/4631 (2013.01)

(56) References Cited

U.S. PATENT DOCUMENTS

| | | | |
|---|---|---|---|
| 7,025,790 | B2 | 4/2006 | Parks et al. |
| 7,238,190 | B2 | 7/2007 | Schon |
| 7,625,409 | B2 | 12/2009 | Saltzman et al. |
| 7,963,996 | B2 | 6/2011 | Sultzman et al. |
| 2007/0073408 | A1 | 3/2007 | Acker et al. |
| 2008/0234688 | A1 | 9/2008 | Johnson et al. |
| 2010/0125240 | A1 | 5/2010 | Spedden et al. |
| 2012/0123553 | A1* | 5/2012 | Sidebotham ........ A61F 2/30771 623/23.15 |
| 2014/0018814 | A1 | 1/2014 | Gillard et al. |
| 2014/0018931 | A1 | 1/2014 | Gillard et al. |

OTHER PUBLICATIONS

"U.S. Appl. No. 13/774,629, Advisory Action dated Oct. 16, 2015", 3 pgs.

"U.S. Appl. No. 13/774,629, Final Office Action dated Aug. 12, 2015", 10 pgs.

"U.S. Appl. No. 13/774,629, Non Final Office Action dated Apr. 23, 2015", 7 pgs.

"U.S. Appl. No. 13/774,629, Notice of Allowance dated Nov. 20, 2015", 7 pgs.

"U.S. Appl. No. 13/774,629, Response filed Feb. 26, 2015 to Restriction Requirement dated Jan. 26, 2015", 5 pgs.

"U.S. Appl. No. 13/774,629, Response filed Apr. 23, 2015 to Non Final Office Action dated Apr. 23, 2015", 15 pgs.

"U.S. Appl. No. 13/774,629, Response filed Oct. 9, 2015 to Final Office Action dated Aug. 12, 2015", 14 pgs.

"U.S. Appl. No. 13/774,629, Restriction Requirement dated Jan. 26, 2015", 8 pgs.

"INBONE II Total Ankle System Surgical Technique", Wright, 36 pgs.

"Salto Talaris Instrumentation II", Tornier, [Online]. Retrieved from Internet: <http://tornierdx.com/pdf/SALTO_SXT_INST2_UJAT092-1oct09-a.pdf>, 36 pgs.

"Total Ankle System The Next step forward in total ankle replacement", Agility LP DePuy, [Online]. Retrieved from the Internet: <http://www.depuy.com/sites/default/files/products/files/DO_Agility_Ankle_LP_Surgtech_0612-50-505.pdf>, (Accessed Feb. 2, 2012), 36 pgs.

\* cited by examiner

ATTACHMENTS FOR ORTHOPEDIC IMPLANTS

CLAIM OF PRIORITY

This patent application is a continuation of U.S. patent application Ser. No. 13/774,629, filed on Feb. 22, 2013, which is a continuation-in-part of U.S. patent application Ser. No. 13/545,119, filed on Jul. 10, 2012, each of which are hereby incorporated by reference herein in its entirety, and the benefit of priority of each of which are hereby claimed.

BACKGROUND

Prosthetic components are available, for example, to replace bodily components or portions of bodily components that cannot be regenerated or are no longer functioning properly. Examples of prosthetic components include heart valves, pacemakers, collagen for soft tissue augmentation, and orthopedic components, such as fracture plates and artificial knee, hip, and ankle joints.

SUMMARY

One aspect of the present disclosure provides a method for attaching a prosthetic component to a bone. This particular method includes a step in which a prosthetic component with an attachment profile is provided. In another step, a mating profile is formed in a bone of a patient. Thereafter, the prosthetic component is positioned adjacent the bone with the attachment profile associating with the mating profile in a male-female mating relationship that leaves at least one open space between the prosthetic component and the bone. In another step, a biocompatible adhesive material is delivered into the at least one open space.

In another aspect, the present disclosure provides a prosthesis that is positionable between a first bone surface and a second bone surface in a patient. The prosthesis includes a first prosthetic component and stackable, second prosthetic component that is stackable onto the first prosthetic component. The first prosthetic component includes a first attachment profile that is associable with a mating profile of the first bone surface in a male-female mating relationship and a second attachment profile that is associable with a mating profile of the second bone surface in a male-female mating relationship. The second prosthetic component includes an attachment profile that replicates the first attachment profile of the first prosthetic component to allow association with the mating profile of the first bone surface in a male-female mating relationship and a mating profile that replicates the mating profile of the first bone surface to allow association with the first attachment profile of the first prosthetic component in a male-female mating relationship.

The present disclosure, in certain other aspects, is directed to apparatus, kits, and methods for the implantation and stabilization of an orthopedic implant to a bone using a filler material such as bone cement. The apparatus, kits, and methods of certain embodiments of the present disclosure can include the use of a cement applicator, such as a syringe, to deliver the bone cement or a cement precursor to one or more desired locations between a prosthetic component of an orthopedic implant and a bone to which the prosthetic component is attached. Use of the cement applicator in such instances allows a surgeon or other medical practitioner to insert, position, align, and attach the prosthetic component prior to the application of bone cement, allowing for appropriate component positioning or alignment and cleaner application of the bone cement, e.g., a bioabsorbable bone cement.

A kit can include a prosthetic component including an attachment profile corresponding to a mating profile formed on or in a bone, and a cement applicator configured to apply a bone cement between the bone and the prosthetic component, following alignment between the prosthetic component and the bone or a second prosthetic component.

A method of implantation can include positioning a prosthetic component adjacent to a bone, aligning the prosthetic component with respect to the bone or with respect to another prosthetic component, or both, and applying a bone cement between the bone and the aligned prosthetic component.

A kit can include a disclosed prosthetic device for positioning adjacent to a bone, aligning with respect to the bone or with respect to another prosthetic device, or both, and attaching to the bone, and cement for applying between the bone and the aligned and attached prosthetic device.

BRIEF DESCRIPTION OF THE DRAWINGS

In the drawings, like numerals can be used to describe similar elements throughout the several views. Like numerals having different letter suffixes can be used to represent different views or instances of similar elements. The drawings illustrate generally, by way of example, but not by way of limitation, various embodiments discussed in the present document.

DETAILED DESCRIPTION

Figure 1:
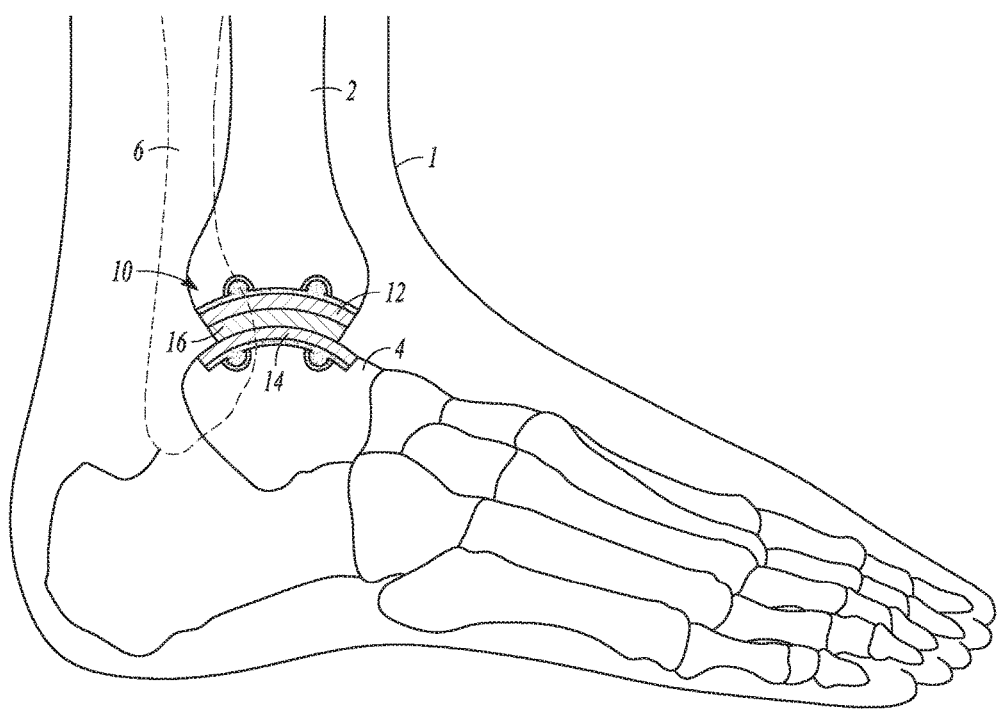
FIG. 1 is a schematic view of an example orthopedic ankle implant positioned in a patient.

The present disclosure, in certain aspects, includes apparatuses, kits, and methods for the implantation and affixing of a prosthetic component of an orthopedic implant to a bone using bone cement. These particular apparatuses, kits, and methods can include the use of a cement applicator, such as a syringe, to deliver a bone cement or a cement precursor to one or more desired locations between a prosthetic component of an orthopedic implant and a bone to which the prosthetic component is attached. Use of the cement applicator can allow a surgeon or other medical practitioner to insert, position, and align the prosthetic component to a bone prior to the application of bone cement. In contrast, existing implantation methods include the application of bone cement, if at all, either to the prosthetic component or to the bone prior to inserting the prosthetic component into the patient, often leading to bone cement being inadvertently spread to unintended or undesirable locations or hardening (e.g., setting) prior to proper component positioning and alignment, all while operating under the timing duress imparted by a limited working time of the cement.

The present apparatus, kits, and methods can provide for the use of less cement and can provide for less cement clean-up compared to existing methods of bone cement application. Additionally, the present apparatus, kits and methods can allow for alignment of the prosthetic component prior to application of the bone cement, thereby allowing for more precise placement and alignment of the prosthetic component. Moreover, because bone cement can be precisely applied using the present cement applicator, the bone cement can be applied to locations that will increase the chances of fixation of the prosthetic component to the bone.

In various examples, the present apparatus, kits, and methods can be used with orthopedic implant systems (e.g., ankle joints, wrist joints, elbow joints, knee joints, hip joints, shoulder joints, finger joints, toe joints, and in a variety of fusion and fusion-type devices including ones utilized in and around the above joints and elsewhere in the skeletal system including in the spine) where bone cement is desirable for fixation and stabilization of a prosthetic component to a bone, particularly when precise application of bone cement is difficult due to space constraints. An example of an orthopedic implant system in which the present apparatus, kits, and methods can be used is an orthopedic ankle implant, such as an implant that may be used for total ankle arthroplasty ("TAA") surgery, also known as total ankle replacement. An ankle implant used for TAA surgery is often inserted through an anterior or lateral ankle arthrotomy. A small portion of bone, such as a small portion of a tibia and/or a talus, can be removed to make room for one or more components of the ankle implant. The portion of bone that is removed from the tibia and/or talus is often only a centimeter or less in thickness, and the implant components to be inserted can be only slightly smaller, if at all, than the vacated space.

FIG. 1 is a schematic view of an example orthopedic ankle implant 10 positioned within a patient 1. Bones located within the leg, foot, and ankle of the patient 1 include the tibia 2, the talus 4, and the fibula 6. The ankle implant 10 can comprise a tibial component 12 and a talar component 14. The tibial component 12 can be affixed to a distal portion of the tibia 2 and the talar component 14 can be affixed to a proximal portion of the talus 4. The ankle implant 10 can further comprise a bearing component, such as a polymeric bearing component 16, positioned between the tibial component 12 and the talar component 14 and providing an articulating surface. An example of a material that can be used to form the bearing component 16 is ultra-high molecular weight polyethylene (UHMWPE). For example, the bearing component 16 can be coupled to the tibial component 12 on a first surface and can articulate against the talar component 14 on a second surface.

An exemplary ankle implant for use with the present apparatuses, kits and methods is shown and described in U.S. Pat. Nos. 7,625,409; 7,963,996; 7,025,790; and 7,238,190, all of which are hereby incorporated by reference in their entirety.

Each of the tibial component 12 and the talar component 14 can comprise an attachment profile or feature(s) corresponding to a mating profile or feature(s) formed in the tibia 2 and the talus 4, respectively. In FIG. 1, for example, the attachment profile of the tibial component 12 is substantially analogous to the mating profile of the tibia 2 allowing the tibial component 12 to fit with the tibia 2 in a keyed arrangement. Similarly, the attachment profile of the talar component 14 can be substantially analogous to the mating profile of the talus 4 allowing the talar component 14 to fit with the talus 4 in a keyed arrangement. The mating profiles of the tibia 2 and the talus 4 can also each include one or more cavities, void spaces, or other female-type mating features in addition to its other mating surfaces. A bone cement can be precisely applied in and/or on the cavities, void spaces, or other features of the mating profile after the components 12, 14 have been inserted into the patient 1 or attached to the tibia 2 or talus 4, respectively, for added stability.

Figure 2:
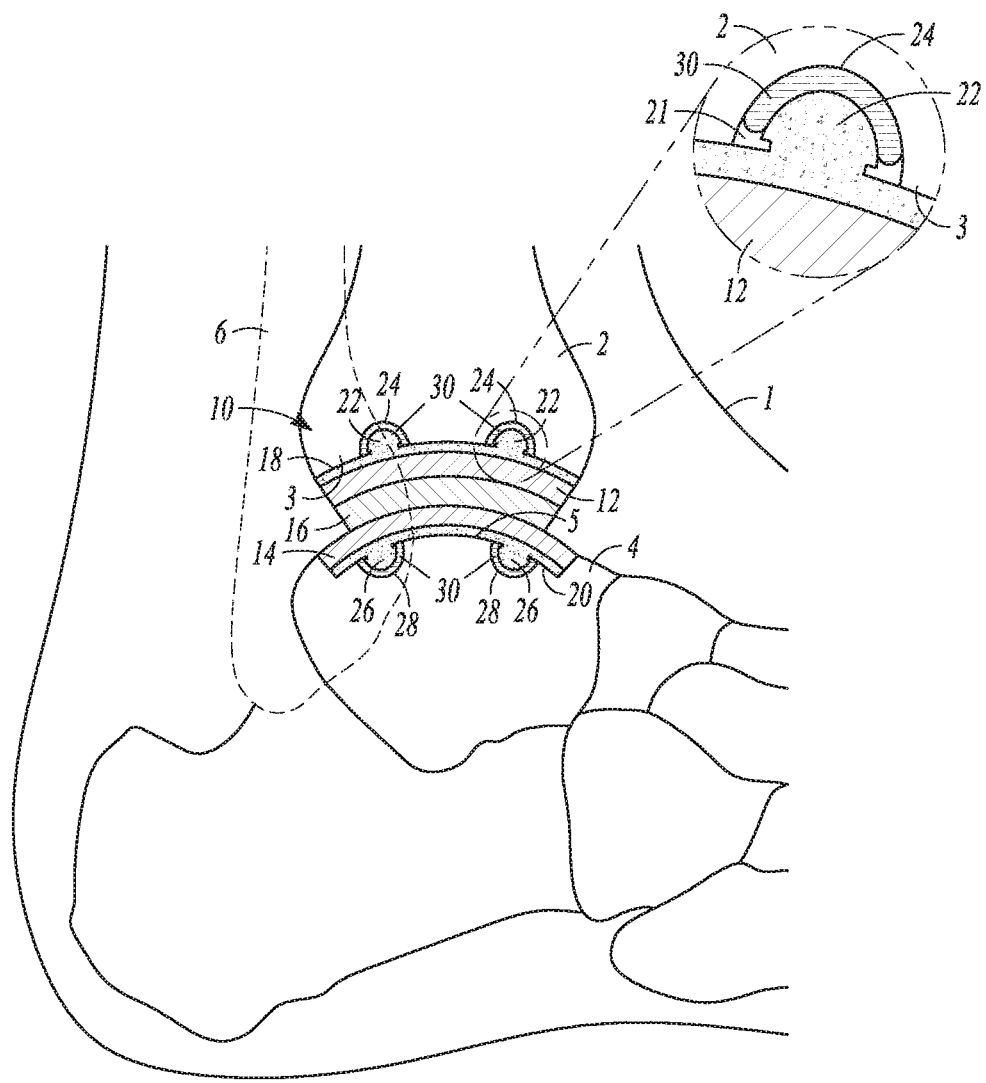
FIG. 2 is a close-up schematic view of an example orthopedic ankle implant having bone cement applied between a bone and a prosthetic component of the orthopedic ankle implant.

FIG. 2 is a close-up schematic view of the example ankle implant 10 of FIG. 1. Prior to insertion of the ankle implant 10, a space can be formed between the tibia 2 and the talus 4 through the manipulation of a tibial distal surface 3 or a talar proximal surface 5, or both. The space can be formed by removing a portion of the tibia 2 to form the distal surface 3 and expose a proximal end of the talus 4, or it can be formed by removing a portion of the talus 4 to form the proximal surface 5 and to expose a distal end of the tibia 2, or both. The tibial component 12 can be inserted into the vacated space so that a proximal surface 18 can be positioned adjacent to the tibial distal surface 3, and the talar component 14 can be inserted into the vacated space so that a distal surface 20 is positioned adjacent to the talar proximal surface 5.

The tibial component 12 can comprise an attachment profile on its proximal surface 18 that can correspond to a mating profile of the tibial distal surface 3. One of the profiles of the tibial component 12 and the tibial distal surface 3 can comprise a male feature and the other can comprise a mating female feature. The attachment profile of the tibial component 12 can include at least one male feature. The male feature can comprise a rail 22 protruding from the proximal surface 18 of the tibial component 12. The mating profile of the tibial distal surface 3 can comprise at least one mating female feature, including a recess 24 sized to receive the projecting rail 22.

Similarly, the talar component 14 can comprise an attachment profile at its distal surface 20 that can correspond to a mating profile of the talar proximal surface 5. One of the profiles of the talar component 14 and the talar proximal surface 5 can comprise a male feature and the other can comprise a mating female feature. The attachment profile of the talar component 14 can include at least one male feature. The male feature can comprise a rail 26 protruding from the distal surface 20 of the talar component 14. The mating profile of the talar proximal surface 5 can comprise at least one mating female feature, including a recess 28 sized to receive the projecting rail 26. Male features other than rails, such as ribs, fins, or keels, can also be used for the tibial component 12, the talar component 14, or both.

The bearing component 16 can be coupled or attached to the tibial component 12 or to the talar component 14. The bearing component 16 can be attached to either component 12, 14 with a mechanical attachment device, such a snap fit between the bearing component 16 and the tibial component 12 or the talar component 14.

Bone cement can be applied between a prosthetic component of an implant and a corresponding bone to which the component is attached. For example, as illustrated in FIG. 2, a bone cement 30 can be applied between the tibial component 12 and the tibia 2, or between the talar component 14 and the talus 4, or both. Using the present teachings, the bone cement 30 can advantageously be applied only to localized, desired locations between each component 12, 14 and the corresponding bone 2, 4. For example, the bone cement 30 can be applied in an interface between male features and female features of the prosthetic components 12, 14 and bones 2, 4. The recesses 24, 28 can be prepared and sized so that they provide space for the rails 22, 26, with additional space to form a cavity for the bone cement 30. Such additional spaces can be shaped and sized in any suitable manner to suit a particular orthopedic application. For example, the female-like void space 21 shown in FIG. 2 substantially mimics the shape of the rail so as to provide a substantially uniform thickness to the void space surrounding the rail. The bone cement 30 can be applied only or substantially only within recesses 24, 28 respectively existing between a projecting rail 22 of the tibial component 12 and the tibial distal surface 3 and between a projecting rail 26 of the talar component 14 and the talar proximal surface 5. This sort of limited and targeted application of bone cement and/or other void-filling biocompatible material at the implantation site can be particularly useful in situations as described herein below where a highly porous, bone ingrowth-receptive material provides bone-contacting surfaces 18, 20 and rails 22, 26. In this regard, the cement or other void-filling material can help to facilitate attachment of the implant to the surrounding bone while also leaving substantial portions of the highly porous, bone-contacting surfaces free of cement or filler and directly open to bone ingrowth.

Figure 3:
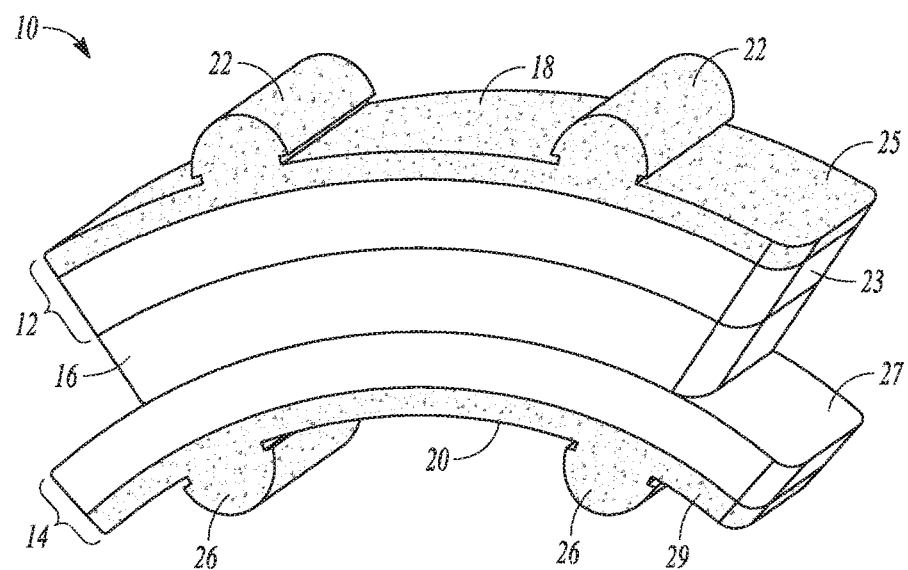
FIG. 3 is an isometric view of an example orthopedic ankle implant.

FIG. 3 is an isometric view of a plurality of components of an ankle implant 10. As illustrated, one or more projecting rails 22 can extend laterally across a proximal surface 18 of a tibial component 12. At least one projecting rail 22 can extend substantially entirely across a lateral width of the tibial component 12. Similarly, one or more projecting rails 26 can extend laterally across a distal surface 20 of the talar component 14. At least one projecting rail 26 can extend substantially entirely across a lateral width of the talar component 14. The ankle implant 10 can further comprise a bearing component 16 positioned between the tibial component 12 and the talar component 14. The bearing component 16 can provide an articulating surface to the ankle implant 10. Other configurations of male features and female features can be used. For example, rather than laterally projecting rails 22, 26, the components 12, 14 can include rails, ribs, fins, or keels that extend from the anterior to the posterior and the corresponding recesses formed in the tibia 12 and the talus 14 can be formed to extend from the anterior to the posterior.

Figure 4:
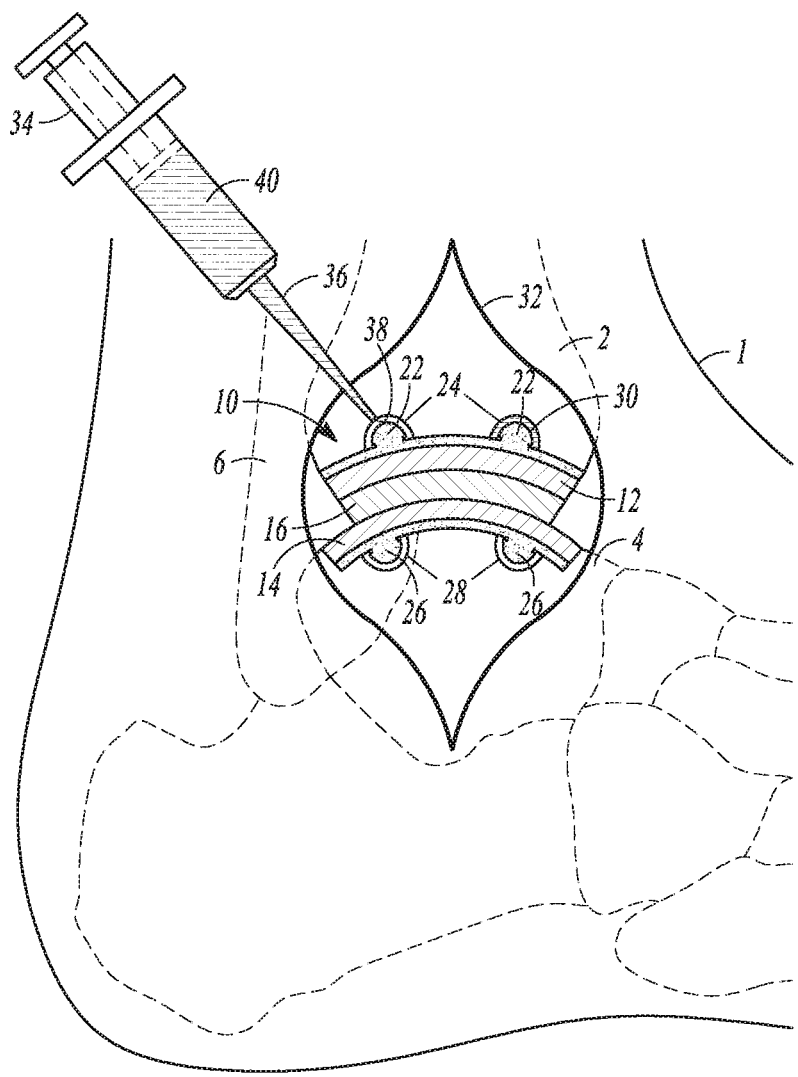
FIG. 4 is a schematic view of an example orthopedic ankle implant having bone cement being applied between a bone and a prosthetic component of the orthopedic ankle implant using a cement applicator.

FIG. 4 is a schematic view of a tibial component 12, a talar component 14, and a bearing component 16 of an ankle implant 10 inserted into a patient 1, such as through an incision 32 in a leg of the patient 1. Bone cement 30 can be locally applied using a cement applicator 34, such as a syringe or a dispenser comprising an applicator nozzle 36, on or in a feature of a prosthetic component or a bone to which the prosthetic component is to be attached. The space between the tibial component 12 and the tibia 2, or between the talar component 14 and the talus 4, or both, can be small, e.g., as small as from 1 millimeter to 2 millimeters. The cement applicator 34 allows a surgeon or other medical practitioner to precisely and locally apply bone cement 30 within the small space, such as in recesses 24, 28 and/or on rails 22, 26. In the example of the ankle implant 10 illustrated in FIG. 4, the cement applicator 34 can be used to apply the bone cement 30 into the recesses 24 to affix the tibial component 12 to the tibia 2 and into the recesses 28 to affix the talar component 14 to the talus 4.

The tibial component 12, the talar component 14, and a bearing component 16, if included, can be inserted into a vacated space between the tibia 2 and the talus 4. Each component 12, 14 can be positioned or aligned with respect to the bone 2, 4 to which it is to be affixed (e.g., so that a position or alignment of the prosthetic component 12, 14 with respect to the bone 2, 4 is substantially similar to a desired final position or alignment) before applying the bone cement 30. For example, after being inserted into the patient 1, the tibial component 12 can be positioned and aligned with respect to the tibia 2 or with respect to the talar component 14. A frame, jig, or other support means can be used to maintain the relative position of the tibial component 12 with respect to the tibia 2 or the talar component 14. The cement applicator 34 can be used to dispense the bone cement 30 into the cavity or space formed between the recesses 24 and the projecting rails 22. Similarly, after being inserted into the patient 1, the talar component 14 can be positioned and aligned with respect to the talus 4 or with respect to the tibial component 12. A frame, jig, or other support means can be used to maintain the relative position of the talar component 14 with respect to the talus 4 or the tibial component 12. The frame, jig, or other support means that is used with the talar component 14 can be the same or different frame, jig, or other support means that is used with the tibial component 12. The cement applicator 34 can be used to dispense the bone cement 30 into the space between the recesses 28 and the projecting rails 26.

In an example, the mating profiles in the tibia 2 and the talus 4 can be formed so that an interference fit can be formed between the attachment profile of the tibial component 12 and the mating profile of the tibia 2, or between the attachment profile of the talar component 14 and the mating profile of the talus 4. An interference fit can allow the components 12, 14 to remain in a desired alignment relative to a corresponding bone 2, 4 without the need of a frame, jig, or other support means. A user can place the component 12, 14 in position and align the component 12, 14 relative to the bone 2, 4, and then engage the component 12, 14 with the bone so that the interference fit can form. The interference fit can then hold the component 12, 14 in place and maintain the alignment until the bone cement 30 can be applied.

For example, an interference fit can be created by forming the recesses 24 and 28 in the tibia 2 and talus 4, respectively, to have a width at one or more positions that is slightly larger than a corresponding width of the corresponding projecting rail 22 or 26. In an example, an interference fit can be formed between a male feature and a female feature if a width at one or more positions of the female feature, such as the recesses 24, 28, is within 0.5 millimeters (mm) (about 0.0197 inches) of a width at a corresponding one or more positions of the male feature, such as the rails 22, 26. The interference fit can also be formed if a width at one or more positions of the female feature is within 0.45 mm (about 0.018 inches), within 04 mm (about 0.0157 inches), within 0.35 mm (about 0.014 inches), within 0.34 mm (0.0134 inches), within 0.33 mm (about 0.13 inches), within 0.32 mm (about 0.0126 inches), within 0.31 mm (about 0.0122 inches), or within 0.3 mm (about 0.0118 inches), such as about 0.28 mm (about 0.011 inches).

The attachment profile or a portion of the attachment profile of the components 12, 14 can also be formed from a material or have a structure that provides for an interference-type of attachment to bone, such as a porous scaffold, for example a porous metal such as porous tantalum. One or more of the rails 22, 26, or at least a portion of the surfaces 18, 20, or both, can be formed from a porous scaffold (e.g., a highly porous scaffold) to facilitate attachment of the components 12, 14 to the tibia 2 and the talus 4, respectively. In an example, substantially all of surfaces 18, 20 and rails 22, 26 can be formed of a porous metal material. The porous metal material can be bonded (e.g., diffusion bonded) or otherwise attached to a metal substrate that forms the remainder of each component 12, 14. For example, as probably best shown in FIG. 3, tibial component 12 in this particular illustrative embodiment, can include a base tibial-side substrate 23 that is fused. (e.g., welded) or otherwise coupled to a highly porous, bone ingrowth-receptive structure 25 which in this instance provides bone-contacting surfaces 18 and rails 22. Likewise, talar component 14 can include abase talar-side substrate 27 that is bonded to a highly porous, bone ingrowth-receptive structure 29 which in this particular instance provides bone-contacting surfaces 20 and rails 26. Examples of materials that can be used to make a substrate (e.g., substrates 23 and 27) to which a porous metal scaffold, such as a porous tantalum scaffold, is coupled include, but are not limited to, titanium (Ti), cobalt-chrome (CoCr), tantalum and alloys thereof such as cobalt chromium molybdenum. According to an exemplary embodiment of the present disclosure, the substrate may be a Ti-6Al-4V alloy, such as Tivanium® which is available from Zimmer, Inc., of Warsaw, Ind. Tivanium® is a registered trademark of Zimmer, Inc.

Highly porous metal structures such as structures 25 and 29 can incorporate one or more of a variety of biocompatible metals. Such structures are particularly suited for contacting bone and soft tissue, and in this regard, can be useful as a bone substitute and as cell and tissue receptive material, for example, by allowing cells and tissue to grow into the porous structure over time to enhance fixation (i.e., osseointegration) between the structure and surrounding bodily structures. Bone cements and other biocompatible void-filling materials disclosed herein can also interdigitate into the pores of these highly porous structures to facilitate attachment of these structures to surrounding bone and/or other implant components. According to certain embodiments of the present disclosure, an open porous metal structure may have a porosity as low as 55%, 65%, or 75% or as high as 80%, 85%, or 90%, or within any range defined between any pair of the foregoing values. An example of an open porous metal structure is produced using Trabecular Metal® Technology available from Zimmer, Inc., of Warsaw, Ind. Trabecular Metal® is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other biocompatible metals may also be used in the formation of a highly porous metal structure such as titanium, a titanium alloy, cobalt chromium, cobalt chromium molybdenum, tantalum, a tantalum alloy, niobium, or alloys of tantalum and niobium with one another or with other metals. It is also within the scope of the present disclosure for a porous metal structure to be in the form of a fiber metal pad or a sintered metal layer, such as a Cancellous-Structured Titanium™ (CSTi™) layer. CSTi™ porous layers are manufactured by Zimmer, of Warsaw, Ind. Cancellous-Structured Titanium™ and CSTi™ are trademarks of Zimmer, Inc.

Generally, a highly porous metal structure will include a large plurality of metallic ligaments defining open voids (i.e., pores) or channels therebetween. The open spaces between the ligaments form a matrix of continuous channels having few or no dead ends, such that growth of soft tissue and/or bone through open porous metal is substantially uninhibited. Thus, the open porous metal may provide a lightweight, strong porous structure which is substantially uniform and consistent in composition, and provides a matrix (e.g., closely resembling the structure of natural cancellous bone) into which soft tissue and bone may grow to provide fixation of the implant to surrounding bodily structures. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

An open porous metal structure may also be fabricated such that it comprises a variety of densities in order to selectively tailor the structure for particular orthopedic applications. In particular, as discussed in the above-incorporated U.S. Pat. No. 5,282,861, an open porous metal structure may be fabricated to virtually any desired density, porosity, and pore size (e.g., pore diameter), and can thus be matched with the surrounding natural tissue in order to provide an improved matrix for tissue ingrowth and mineralization. According to certain embodiments, an open porous metal structure may be fabricated to have a substantially uniform porosity, density, and/or void (pore) size throughout, or to comprise at least one of pore size, porosity, and/or density being varied within the structure. For example, an open porous metal structure may have a different pore size and/or porosity at different regions, layers, and surfaces of the structure. The ability to selectively tailor the structural properties of the open porous metal, for example, enables tailoring of the structure for distributing stress loads throughout the surrounding tissue and promoting specific tissue ingrown within the open porous metal.

In other embodiments, an open porous metal structure may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of an open porous metal structure may comprise a metal substrate combined with a Ti-6Al-4V powder and a ceramic material, which is sintered under heat and pressure. The ceramic particles may thereafter be removed leaving voids, or pores, in the substrate. An open porous metal structure may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of an open porous metal structure may comprise a porous metal substrate having particles, comprising altered geometries, which are sintered to a plurality of outer layers of the metal substrate. Additionally, an open porous metal structure may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

Examples of porous scaffolds for prosthetic implants, such as orthopedic bone restoration or joint repair implants, are described in the aforementioned U.S. Pat. No. 5,282,861 to Kaplan, entitled "Open Cell Tantalum Structures For Cancellous Bone Implants and Cell and Tissue Receptors," and U.S. Provisional Patent Application Ser. No. 61/653,510, entitled "ANISOTROPIC POROUS SCAFFOLDS," filed on May 31, 2012, which are incorporated herein by reference in their entireties. A porous scaffold is available under the aforementioned trade name TRABECULAR METAL™ from Zimmer, Inc., Warsaw, Ind., USA, such as for orthopedic implants. The porous structure of a porous scaffold can also provide for cement adhesion to the components 12, 14.

The cement applicator 34 can comprise a needle or nozzle 36 having a small cross-sectional width at a tip 38, thereby allowing the tip 38 and a portion of the needle or nozzle 36 to fit within a profile feature of either a prosthetic component, such as the tibial component 12 or the talar component 14, or a bone to which the prosthetic component is to be attached, such as the tibia 2 or the talus 4. In an example, the needle or nozzle 36 is sized and shaped to fit into a recess formed between male and female features, such as between one of the rails 22 of the tibial component 12 and a corresponding recess 24 within the tibia 2. The needle or nozzle 36 can also be sized and shaped for insertion into a first lateral end of a recess 24, 28 and across the desired width to a medial end of the recess 24, 28.

In addition to, or as an alternative to bone cement 30, a variety of bioabsorbable and non-bioabsorbable void-filling materials can be delivered to recesses and other open spaces or voids that are provided adjacent a prosthetic component as disclosed herein such as recesses 24, 28. Illustratively, the bone cement 30 can be any adhesive material configured for adequately stabilizing a prosthetic component to a bone. An example bone cement is a polymeric bone cement, such as a polymethyl methacrylate ("PMMA") cement. The bone cement 30 can be formed from a cement precursor 40 comprising one or more materials that undergo polymerization or cross-linking to form a solid or substantially solid bone cement 30, when cured. The cement precursor 40 can be formed by mixing a liquid monomer with a particulate or powdered copolymer. After the liquid monomer and the copolymer are mixed and applied, the liquid monomer can undergo a polymerization reaction, such as a free-radical polymerization, to form the solid or substantially solid cement 30.

A liquid monomer that can be used is, but is not limited to, methyl methacrylate monomer. Examples of a particulate or powdered copolymer can include, but are not limited to, polymethyl methacrylate and methyl methacrylate-styrene. Other compounds, such as a polymerization initiator or a polymerization accelerator, can be mixed with the liquid monomer and the particulate or powdered copolymer when forming the cement precursor 40.

After being formed, the bone cement 30 or cement precursor 40 can be loaded into the cement applicator 34 and dispensed between a prosthetic component and a bone. In an example, the cement precursor 40 begins polymerizing, or setting, soon after the liquid polymer and the particulate or powdered copolymer are mixed. Alternatively, the cement precursor 40 can remain substantially in liquid form for a period of time sufficient to apply it in desired void locations using the cement applicator 34. In various examples, the materials forming the cement precursor 40 are selected so that the bone cement 30 will not set (e.g., will not be fully polymerized) for from about 3 minutes to about 5 minutes after mixing. The bone cement 30 or cement precursor 40 can have a viscosity conducive to its application from a needle or nozzle 36 having a profile or cross section that is sized and shaped to fit into a recess formed between male and female features, such as between one of the rails 22 of the tibial component 12 and a corresponding recess 24 within the tibia 2. In an example, the cement precursor 40 is configured so that the viscosity of the cement precursor 40 remains below a threshold viscosity for at least a period of time that is sufficient to apply the cement precursor 40 through the cement applicator 34 into one or more desired locations, such as within a recess 24, 28. In an example, the cement precursor 40 has a viscosity below the threshold viscosity for from about 3 minutes to about 5 minutes after the cement precursor 40 is formed.

The threshold viscosity that is acceptable can depend on several factors, including the geometry of the cement applicator 34, the geometry of the needle or nozzle 36 and the tip 38, the geometry of the space into which the bone cement 30 or cement precursor 40 is to be applied, and the physical makeup of the bone cement 30 or cement precursor 40 (e.g., the particle size of the copolymer, the weight percent of the copolymer in the cement precursor mixture, or the composition and weight percent of additives in the cement precursor mixture).

An example of a suitable bone cement 30 that can be used is OSTEOBOND® copolymer bone cement, manufactured by Zimmer, Inc., of Warsaw, Ind., USA.

The prosthetic component or components described herein, such as the tibial component 12 and the talar component 14, can be combined in a kit with a cement applicator configured to apply a bone cement between the bone and the prosthetic component, following alignment of the prosthetic component with the bone, or engagement between the attachment profile of the prosthetic component and the mating profile of the bone, or both. The kit can also include a separate or integral sterile package for one or more of the kit components, such as the prosthetic component or components and the cement applicator. The kit can also comprise a bone cement or a cement precursor to be applied between the bone and the prosthetic component. The kit can also comprise a frame configured to maintain a position or an alignment of the prosthetic component with respect to the bone or with respect to a second prosthetic component. The kit can also include instructions for a user, such as to perform some or all of the steps of the method or methods described below.

Figure 5:
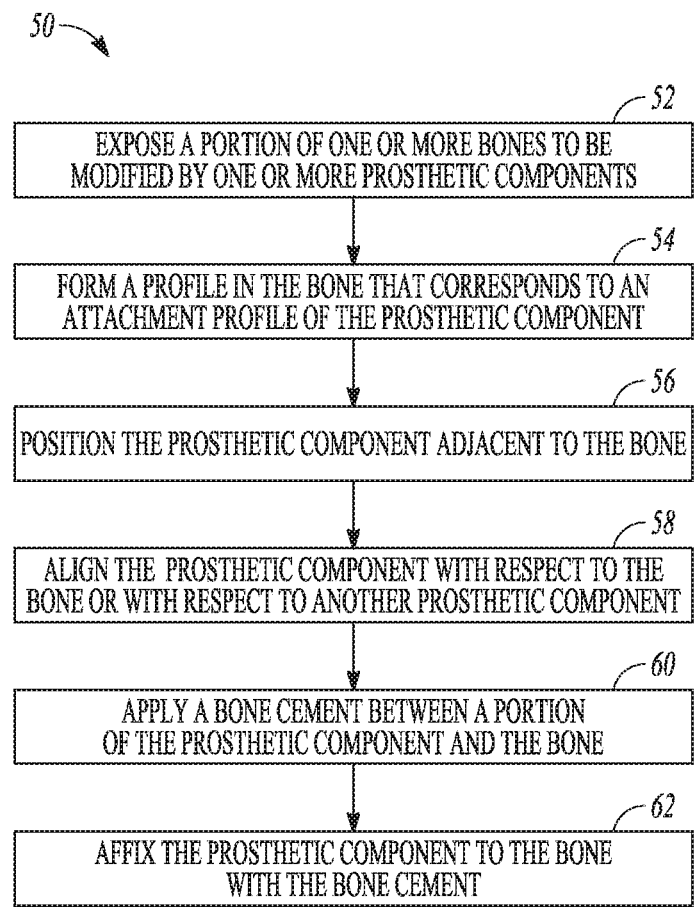
FIG. 5 is a flow chart of an example method of implanting an example prosthetic component.

FIG. 5 is a flow chart of an example method 50 of affixing a prosthetic component, such as a tibial or talar component of an orthopedic ankle implant, to a bone, such as a tibia or a talus. The method 50 can comprise, at 52, exposing a portion of one or more bones to be modified (e.g., the tibia and the adjacent talus) by one or more prosthetic components, such as by cutting through the skin, muscle, and other tissue of a patient. At 54, a profile in the bone can be formed to mate with an attachment profile of the prosthetic component. The profile in the bone can be a reverse or mirror image of the attachment profile of the prosthetic component. Forming the profile can comprise forming a feature in the bone that corresponds to a feature of the attachment profile of the prosthetic component, such as forming a female feature in the bone, such as a recess, configured to receive or mate with a male feature of the prosthetic component, such as a projecting rail, a fin, a rib, or a keel.

At 56, the prosthetic component can be positioned adjacent to the bone, and, at 58, the prosthetic component can be aligned with respect to the bone or with respect to another prosthetic component. Positioning or aligning the prosthetic component allows a user to assure that an alignment or position of the prosthetic component with respect to the bone or with respect to the other prosthetic component is substantially the same as a desired final position or alignment of the prosthetic component, such as the desired position or alignment of the tibial component with respect to the tibia or the talar component after affixing the tibial component to the tibia. Positioning the prosthetic component can comprise inserting the prosthetic component into the patient, for example through an incision. Positioning the prosthetic component can also comprise engaging an attachment profile of the prosthetic component with the corresponding mating profile of the bone. The term "engaging," as used herein with respect to a prosthetic component and a corresponding bone, can refer to positioning one or more features of the attachment profile of the prosthetic component so that they are in substantially the same position as a corresponding mating feature or features of the profile of the bone. For example, the prosthetic component can be positioned so that the attachment profile fits with the bone in a keyed relationship. As shown in the ankle implant of FIGS. 1-4, the attachment profile of the tibial component can comprise one or more male features in the form of projecting rails, and the mating profile of the tibia can comprise a corresponding recess for each projecting rail.

After positioning or aligning the prosthetic component, or both, the method 50 can include, at 60, a bone cement can be applied between a portion of the positioned or aligned prosthetic component and the bone. Application of the bone cement can comprise dispensing a cement precursor into a void between the attachment profile of the prosthetic component and the mating profile of the bone. The cement precursor can be applied in or on a feature of the bone, or in or on a feature of the prosthetic component, or both. At 62, the prosthetic component can be affixed to the bone with the bone cement. The bone cement can be passively allowed to set or harden in order to affix the prosthetic component to the bone, or the bone cement can be actively set, such as with an activatable initiator, such as a photoinitiator.

Application of the bone cement can comprise injecting or dispensing the cement precursor with a cement applicator, such as the example applicator illustrated in FIG. 4. The cement applicator can be configured to dispense the cement precursor to a localized and desired location, such as between a rail of the tibial component and a recess in the tibia through a nozzle or a needle conduit and with little to no cement leakage. The cement applicator can allow for the application of the cement precursor after the tibial component, for example, has been inserted into the patient, positioned with respect to the tibia or the talar component, aligned with respect to the tibia or the talar component, yet still ensure that the cement precursor and the resulting bone cement is adequately applied at desired locations.

Application of the cement precursor between the prosthetic component and the bone to which the prosthetic component is to be attached can comprise substantially filling a female feature of the prosthetic component and/or the bone with the cement precursor. In an example where a female feature comprises a recess, the method can comprise filling the recess substantially across an entire medial length of the recess with the cement precursor. Each female feature can be filled using a retrograde fill method. "Retrograde filling" can refer to a method where the bone cement or cement precursor is dispensed as the applicator is withdrawn from the female feature, such as by inserting the nozzle of the applicator into a first lateral end of the recess and across the lateral width of the recess to a second lateral end of the recess, followed by withdrawing the nozzle from the recess while concurrently dispensing the cement precursor through the nozzle. In an example, the cement precursor can be dispensed or prepared so that the female feature is substantially free of entrapped air.

The method 50 can further comprise forming the cement precursor prior to dispensing. Forming the cement precursor can comprise mixing a liquid monomer, such as methyl methacrylate, with a particulate or powdered copolymer, such as a powdered polymethyl methacrylate or a powdered methyl methacrylate-styrene. Other additives can be mixed with the monomer and the copolymer, such as a polymerization initiator or a polymerization accelerator. Mixing the liquid monomer and the particulate or powdered copolymer can result in a polymerization reaction, such as free-radical polymerization, to form a solid or substantially solid bone cement.

The method 50 can comprise loading the cement precursor into the cement applicator. In an example, loading the cement precursor into the cement applicator can include removing or evacuating any air from the cement applicator, such as by inverting the cement applicator and then dispensing the air and a small amount of the cement precursor from the cement applicator prior to applying the cement precursor between the prosthetic component and the bone.

After applying the cement precursor between the prosthetic component and the bone, the method 50 can further comprise removing excess cement precursor or bone cement so that the excess bone cement does not interfere with operation of the implant or contaminate the surgical site. After the bone cement has set, stability, strength, or both, of the bone cement and the prosthetic component can be tested.

Figure 6:
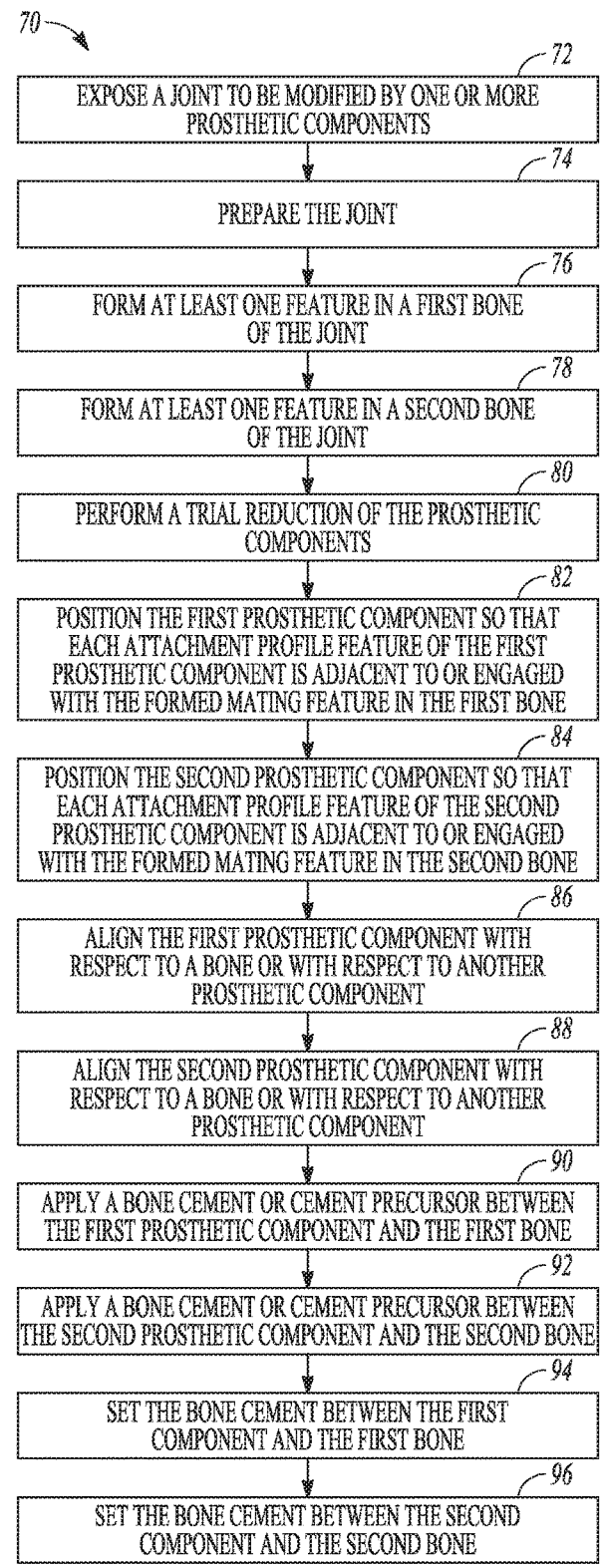
FIG. 6 is a flow chart of an example method of implanting an orthopedic ankle implant including two or more prosthetic components.

FIG. 6 is a flow chart of an example method 70 of positioning an orthopedic ankle implant, for example, into a patient, to replace a joint. At 72, a joint that is to be modified by one or more prosthetic components can be exposed. Exposing the ankle joint can comprise cutting through the patient's skin, muscle, and other tissue, and resecting and pulling back bodily tissue.

At 74, the joint can be prepared for modification, such as by cleaning out extraneous material or tissue. Preparing the joint can also include removing a portion of one or more bones, such as the tibia and the talus, in order to make room for one or more prosthetic components of the implant. Removing portions of the one or more bones can include stabilizing a patient's extremity of interest using a frame, jig, or other support apparatus, followed by cutting or resecting a portion of one or more of the bones.

At 76, at least one feature can be formed in a first bone of the joint. At 78, at least one feature can be formed in a second bone of the joint. Each feature that is formed can correspond to an attachment feature of a corresponding prosthetic component.

At 80, a trial reduction of the prosthetic components can be performed, such as by inserting a temporary or trial version of each component of the final prosthetic implant into the patient to test for an acceptable size and geometry. In the case of an ankle implant, for example, a trial tibial component with a geometry similar to that of a final tibial component, a trial talar component with a geometry similar to that of a final talar component, and a trial bearing component with a geometry similar to that of a final bearing component can be inserted into the patient, positioned, and aligned in much the same way that final components can be aligned. A surgeon or other medical practitioner can then inspect the trial components and the corresponding bones to determine if the fit and alignment of the trial components is acceptable (e.g., ensuring that there is no lateral overhang of the trials beyond the tibia or the talus, ensuring that there is no bony impingement by the fibula, ensuring that the trial tibial component is substantially flush with the tibia, or ensuring that the trial talar component is substantially flush with the talus). If the fit or alignment of the trial components is not acceptable, the trial components can be removed, and one or more trial components of a different size or shape can be inserted or the bones can be further manipulated.

At 82, a first prosthetic component can be positioned in the patient so that each attachment profile feature of the first prosthetic component is adjacent to, or engaged with, a corresponding formed mating profile feature in the first bone. Similarly, at 84, a second prosthetic component can be positioned in the patient so that each attachment profile feature of the second prosthetic component is adjacent to, or engaged with a corresponding formed mating profile feature in the second bone. The first and second final prosthetic components that are selected and positioned within the patient can each have a geometry that is identical or substantially identical to a geometry of the corresponding component that was found to provide for an acceptable fit during the trial reduction, at 80.

At 86, the first prosthetic component can be aligned with respect to a bone, such as the first bone, or with respect to another prosthetic component, such as the second prosthetic component. Similarly, at 88, the second prosthetic component can be aligned with respect to a bone, such as the second bone, or with respect to another prosthetic component, such as the first prosthetic component. In the case of the ankle implant, for example, the tibial component can be aligned with respect to the tibia, with respect to the talar component, or with respect to the bearing component. Similarly, the talar component can be aligned with respect to the talus, with respect to the tibial component, or with respect to the bearing component. Aligning each component can comprise securing each component with one or more frames, jigs, or other securing apparatus to adjust and maintain the alignment of each component.

At 90, a bone cement or a cement precursor can be applied between the first prosthetic component and the first bone and. Similarly, at 92, the bone cement or the cement precursor can be applied between the second prosthetic component and the second bone. In the case of the ankle implant, for example, the bone cement or the cement precursor can be applied between the tibial component and the tibia or between the talar component and the talus.

At 94, the bone cement between the first prosthetic component and the first bone can be set in order to affix the first prosthetic components to the first bone. Similarly, at 96, the bone cement between the second prosthetic component and the second bone can be set in order to affix the second prosthetic component to the second bone. Setting the bone cement can comprise allowing the bone cement to set without active steps (e.g., allowing a cement precursor to polymerize and set as a solid or substantially solid bone cement to set). Alternatively, setting the bone cement can comprise actively causing or initiating setting via the use of a heat-activated cement precursor that begins setting upon the application of heat above an activation temperature or an ultraviolet-activated cement precursor that begins setting upon exposure to ultraviolet light of specified wavelength. While the cement precursor is setting to form the bone cement, the position and alignment of the prosthetic components with respect to the bones can be maintained, such as through continued use of a frame, jig, or other securing apparatus that holds one or more prosthetic components in position or alignment with respect to one or more bones or one or more other prosthetic components.

The steps of the method 70 can generally be performed in any order, except where the ordering of steps is necessitated. For example, although the flow diagram of FIG. 6 illustrates, at 76, forming at least one feature in the first bone before forming at least one feature in the second bone, at 78, these steps can be performed in a reverse order. Moreover, each step involving the first prosthetic component and the first bone can be performed in their entirety without performing the steps involving the second prosthetic component and the second bone, and vice versa. For example, a method can comprise, at 76, forming at least one feature in the first bone, e.g., the tibia, corresponding to at least one mating feature in the first prosthetic component, e.g., the tibial component, then, at 82, positioning the tibial component, e.g., adjacent to or engaged with the tibia, then, at 86, aligning the tibial component with respect to the tibia or with respect to another prosthetic component, then, at 90, applying a bone cement or cement precursor between the tibial component and the tibia, then, at 94, setting the bone cement between the tibial component and the tibia. After completing these method steps with respect to the first prosthetic component, the method can then include performing the steps with respect to the second prosthetic component, e.g., at 78, forming at least one feature in the second bone, e.g., the talus, corresponding to at least one mating feature of the second prosthetic component, e.g., the talar component, then, at 84, positioning the talar component, e.g., adjacent to or engaged with the talus, then, at 88, aligning the talar component with respect to the talus or with respect to another prosthetic component, then, at 92, applying a bone cement or cement precursor between the talar component and the talus, then, at 96, setting the bone cement between the talar component and the talus.

Figure 7:
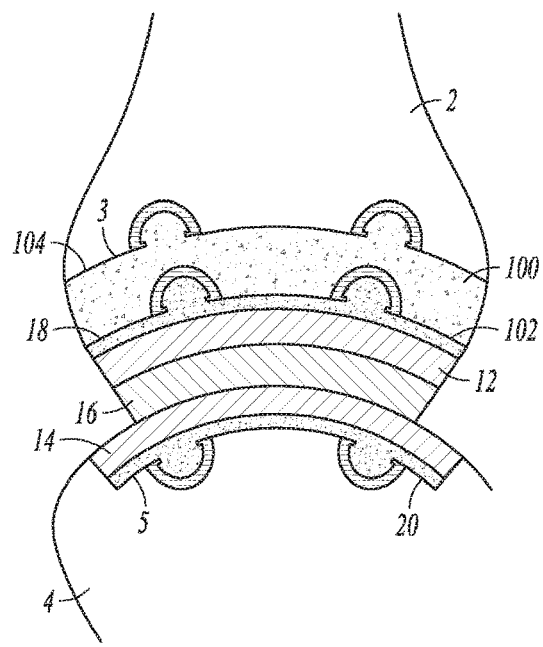
FIG. 7 is a close-up schematic view of another example orthopedic ankle implant.

With reference now to FIG. 7, shown is an example ankle implant similar to that shown in FIG. 2 except additionally incorporating a stackable member 100 stacked atop tibial component 12. Stackable member 100 can be formed with a variety of biocompatible implant materials, and in this particular illustrative embodiment is formed with a highly porous metallic material that is particularly adapted to receive bony ingrowth. Illustratively, at this particular treatment site, the tibial component 12 includes an attachment profile on its proximal surface 18 that corresponds to a mating profile of a distal surface 102 of the stackable member 100, whereas the stackable member 100 includes an attachment profile on its proximal surface 104 that corresponds to a mating profile of the tibial distal surface 3. As discussed herein above, such profiles can incorporate cooperating male and female features. Male or male-type elements can include rails, ribs, fins, keels, and other projections. In this instance, male-type rails similar to rails 22 shown in FIG. 2 protrude from tibial component proximal surface 18 and from stackable member proximal surface 104. Female-type recesses are located in stackable member distal surface X and in tibial distal surface 3 for accommodating the rails while leaving additional space to form a cavity for bone cement and/or another biocompatible filler material as similarly discussed elsewhere herein.

The talar component 14 is similar to that shown in FIG. 2, and includes an attachment profile with projecting rails at its distal surface 20. These rails can be received in recesses in the talar proximal surface 5 where the recesses can provide space for the rails with additional space for filler material(s). In an alternative embodiment, a second stackable member (not shown) can be stacked below talar component 14. Such a member can be similar to member 100 except being matable with the distal surface of the talar component 14 including its rails and with the talar proximal surface 5 including its recesses. This second stackable member can be incorporated into the overall implant in addition to or instead of stackable member 100, and in this regard, it will be understood that, to suit a particular orthopedic application, any suitable number of successive stackable members can be stacked adjacent tibial component 12 and/or talar component 14. Also, any two such stackable members in an implant arrangement can be the same or different in terms of physical characteristics such as but not limited to shape, size, thickness, and material(s) of construction.

Figure 8:
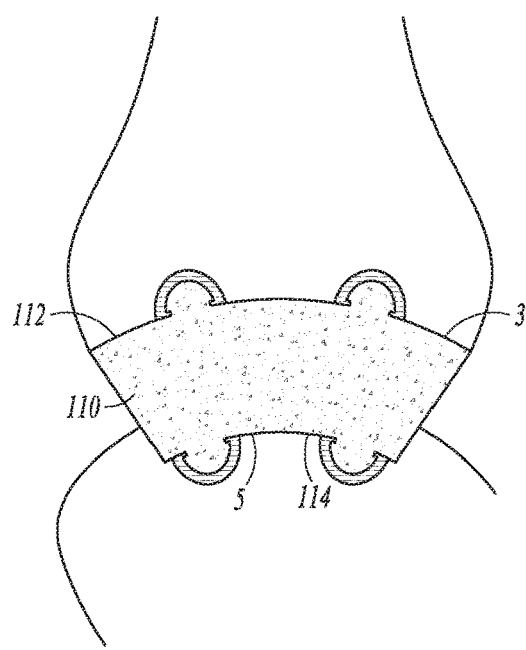
FIG. 8 is a close-up schematic view of an example ankle fusion device.

With reference now to FIG. 8, shown is an example of an ankle fusion device 110 according to one embodiment of the present disclosure. This and other fusion devices disclosed herein could be similar adapted for use elsewhere in the skeletal system including but not limited to in the foot, hand, and spine. This particular fusion device is formed with a highly porous metallic material that is particularly adapted to receive bony ingrowth although it can be formed with any number of suitable fusion-facilitating materials. Illustratively, at this particular treatment site, the fusion device 110 includes an attachment profile on its proximal surface 112 that corresponds to a mating profile of the tibial distal surface 3 and an attachment profile on its distal surface 114 that corresponds to a mating profile of the talar proximal surface 5. As discussed herein above, such profiles can incorporate cooperating male and female features. Male or male-type elements can include rails, ribs, fins, keels, and other projections. In this instance, male-type rails similar to rails 22 shown in FIG. 2 protrude from fusion device proximal surface 112 and from distal surface 114. Female-type recesses are located in tibial distal surface 3 and talar proximal surface 5 for accommodating the rails while leaving additional space to form a cavity for bone cement and/or another biocompatible filler material as similarly discussed elsewhere herein.

In an alternative embodiment, one or more stackable members (not shown) similar to the stackable members discussed above in relation to FIG. 7 can be stacked atop fusion device proximal surface 112 and/or one or more stackable members can be stacked below fusion device distal surface 114 to provide a stacked, multi-part fusion device. Any suitable number of stackable fusion members can be employed in this regard to suit a particular orthopedic application. Illustratively, a first stackable member can be stacked atop fusion device proximal surface 112 with the attachment profile of this proximal surface corresponding to a mating profile of a distal surface of the first stackable member. The first stackable member can then include an attachment profile on its proximal surface that corresponds to a mating profile of the tibial distal surface 3. As discussed herein above, such profiles can incorporate a variety of cooperating male and female features including but not limited to rails and rail-accommodating recesses as shown in FIG. 8. Any two such stackable members in a stacked, multi-part fusion arrangement can be the same or different in terms of physical characteristics such as but not limited to shape, size, thickness, and material(s) of construction.

To better illustrate the apparatus, kits, and methods and disclosed herein, a non-limiting list of examples is provided here:

Example 1 can include subject matter (such as an apparatus, a device, a method, or one or more means for performing acts), such as can include a kit. The subject matter can comprise a prosthetic component including an attachment profile corresponding to a mating profile formed on or in a bone, and a cement applicator configured to apply a bone cement between the bone and the prosthetic component, following alignment between the prosthetic component and the bone or another prosthetic component.

Example 2 can include, or can optionally be combined with the subject matter of Example 1, to optionally include the prosthetic component being a first prosthetic component and the bone being a first bone.

Example 3 can include, or can optionally be combined with the subject matter of one or any combination of Examples 1 or 2, to optionally include a second prosthetic component including an attachment profile corresponding to a mating profile formed in a second bone.

Example 4 can include, or can optionally be combined with the subject matter of one or any combination of Examples 1-3, to optionally include the first prosthetic component and the second prosthetic component forming at least a portion of a prosthetic joint.

Example 5 can include, or can optionally be combined with the subject matter of one or any combination of Examples 1-4, to optionally include the prosthetic joint includes at least one of a prosthetic ankle joint, a prosthetic wrist joint, a prosthetic elbow joint, a prosthetic knee joint, a prosthetic hip joint, a prosthetic shoulder joint, a prosthetic finger joint, and a prosthetic toe joint.

Example 6 can include, or can optionally be combined with the subject matter of one or any combination of Examples 1-5, to optionally include the cement applicator including a conduit sized and shaped to apply the bone cement into a void between the bone and the prosthetic component.

Example 7 can include, or can optionally be combined with the subject matter of one or any combination of Examples 1-6, to optionally include a frame configured to maintain a position or an alignment of the prosthetic component with respect to the bone or with respect to a second prosthetic component.

Example 8 can include, or can optionally be combined with the subject matter of one or any combination of Examples 1-7, to optionally include one or more components of the bone cement to be loaded into the cement applicator.

Example 9 can include, or can optionally be combined with the subject matter of one or any combination of Examples 1-8, to optionally include a precursor of the bone cement including a liquid monomer and a particulate copolymer.

Example 10 can include, or can optionally be combined with the subject matter of one or any combination of Examples 1-9, to optionally include instructions for using the prosthetic component and the cement applicator.

Example 11 can include, or can optionally be combined with the subject matter of one or any combination of Examples 1-10, to optionally include the instructions reciting the steps of positioning the prosthetic component adjacent to the bone, aligning the prosthetic component with respect to the bone or with respect to another prosthetic component, and applying the bone cement between the bone and the aligned prosthetic component.

Example 12 can include, or can optionally be combined with the subject matter of one or any combination of Examples 1-11, to optionally include the instructions further reciting forming the mating profile in the bone by forming a male projecting feature or a female receiving feature.

Example 13 can include, or can optionally be combined with the subject matter of one or any combination of Examples 1-12, to optionally include the instructions for applying the bone cement reciting applying the bone cement onto the male projecting feature or into the female receiving feature after aligning the prosthetic component with respect to the bone or with respect to the other prosthetic component.

Example 14 can include, or can optionally be combined with the subject matter of one or any combination of Examples 1-13, to optionally include the instructions further reciting a step of maintaining the alignment of the prosthetic component with respect to the bone or with respect to the other prosthetic component while applying the bone cement between the prosthetic component and the bone.

Example 15 can include, or can optionally be combined with the subject matter of one or any combination of Examples 1-14, to include subject matter (such as an apparatus, a device, a method, or one or more means for performing acts), such as can include a method of implant. The subject matter can include positioning a prosthetic component adjacent to a bone, aligning the prosthetic component with respect to the bone or with respect to another prosthetic component, and applying a bone cement between the bone and the aligned prosthetic component.

Example 16 can include, or can optionally be combined with the subject matter of one or any combination of Examples 1-15, to optionally include forming a bone feature on or in the bone, wherein the bone feature corresponds to an attachment profile of the prosthetic component.

Example 17 can include, or can optionally be combined with the subject matter of one or any combination of Examples 1-16, to optionally include the forming the bone feature including forming a male projecting feature or a female receiving feature.

Example 18 can include, or can optionally be combined with the subject matter of one or any combination of Examples 1-17, to optionally include the applying the bone cement including applying the bone cement onto the male projecting feature or into the female receiving feature after aligning the prosthetic component with respect to the bone or with respect to the other prosthetic component.

Example 19 can include, or can optionally be combined with the subject matter of one or any combination of Examples 1-18, to optionally include the applying the bone cement including injecting the bone cement through a conduit of a cement applicator and into or around a void between the bone and the aligned and attached prosthetic component.

Example 20 can include, or can optionally be combined with the subject matter of one or any combination of Examples 1-19, to optionally include the applying the bone cement including applying the bone cement in a retrograde direction.

Example 21 can include, or can optionally be combined with the subject matter of one or any combination of Examples 1-20, to optionally include the attaching the prosthetic component to the bone including forming at least a portion of a prosthetic joint selected from a prosthetic ankle joint, a prosthetic wrist joint, a prosthetic elbow joint, a prosthetic knee joint, a prosthetic hip joint, a prosthetic shoulder joint, a prosthetic finger joint, and a prosthetic toe joint.

Example 22 can include, or can optionally be combined with the subject matter of one or any combination of Examples 1-21, to optionally include forming the bone cement, including mixing a monomer and a particulate copolymer or a cement powder.

Example 23 can include, or can optionally be combined with the subject matter of one or any combination of Examples 1-22, to optionally include maintaining the alignment of the prosthetic component with respect to the bone or with respect to the other prosthetic component while applying the bone cement between the bone and the prosthetic component.

Example 24 can include, or can optionally be combined with the subject mat er of one or any combination of Examples 1-23, to include subject matter (such as an apparatus, a device, a method, or one or more means for performing acts), such as can include a kit. The subject matter can include a prosthetic device for positioning adjacent to a bone and aligning with respect to the bone or with respect to another prosthetic device, and cement for applying between the bone and the aligned prosthetic device.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, kit, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the detailed description, with each claim standing on its own as a separate embodiment. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A prosthesis positionable between a first bone surface and a second bone surface in a patient, comprising:
    a first prosthetic component with a first attachment profile that is associable with a mating profile of the first bone surface in a male-female mating relationship and a second attachment profile that is associable with a mating profile of the second bone surface in a male-female mating relationship; and
    a stackable, second prosthetic component stackable onto the first prosthetic component, the second prosthetic component including an attachment profile that replicates the first attachment profile of the first prosthetic component to allow association with the mating profile of the first bone surface in a male-female mating relationship and a mating profile that replicates the mating profile of the first bone surface to allow association with the first attachment profile of the first prosthetic component in a male-female mating relationship.

2. The prosthesis of claim 1, wherein the second component is stackable onto the first prosthetic component so that the male-female mating relationship between the mating profile of the second prosthetic component and the first attachment profile of the first prosthetic component leaves at least one open space between the first prosthetic component and the second prosthetic component.

3. The prosthesis of claim 2, further comprising a biocompatible adhesive material located in said at least one open space.

4. The prosthesis of claim 3, wherein the biocompatible adhesive material is absorbable.

5. The prosthesis of claim 1, wherein a highly porous metallic component provides the first attachment profile of the first prosthetic component.

6. The prosthesis of claim 5, wherein a second highly porous metallic component provides the second prosthetic component.

7. The prosthesis of claim 1, wherein the first prosthetic component is a prosthetic joint.

8. The prosthesis of claim 7, wherein the first prosthetic component is a prosthetic ankle joint with a tibial component providing the first attachment profile and a talar component providing the second attachment profile.

9. The prosthesis of claim 1, wherein the first prosthetic component is a fusion device.

10. The prosthesis of claim 9, wherein the first prosthetic component and the second prosthetic component are both formed with a highly porous metallic material.

* * * * *